(12) United States Patent
Gorbunov et al.

(10) Patent No.: US 11,185,246 B2
(45) Date of Patent: Nov. 30, 2021

(54) SMART WATCH STRAP FOR BIOIMPEDANCE MEASUREMENTS

(71) Applicant: AURA Devices, Inc., Wilmington, DE (US)

(72) Inventors: Stanislav Gorbunov, Moscow (RU); Igor Dorokhin, Saratov (RU); Dmitrii Davydov, Lublin (PL); Andrey Boev, Stariy Oskol (RU)

(73) Assignee: AURA DEVICES, INC., Wilmington, DE (US)

( * ) Notice: Subject to any disclaimer, the term of this patent is extended or adjusted under 35 U.S.C. 154(b) by 0 days.

(21) Appl. No.: 16/548,856

(22) Filed: Aug. 23, 2019

(65) Prior Publication Data

US 2021/0052188 A1 Feb. 25, 2021

(51) Int. Cl.
*A61B 5/0531* (2021.01)
*A61B 5/00* (2006.01)
*A61B 5/0537* (2021.01)

(52) U.S. Cl.
CPC ............ *A61B 5/0531* (2013.01); *A61B 5/681* (2013.01); *A61B 5/6831* (2013.01); *A61B 5/0537* (2013.01); *A61B 5/6824* (2013.01); *A61B 5/6844* (2013.01); *A61B 5/7225* (2013.01); *A61B 2560/0238* (2013.01); *A61B 2560/0406* (2013.01); *A61B 2560/0468* (2013.01); *A61B 2562/0214* (2013.01); *A61B 2562/0233* (2013.01); *A61B 2562/043* (2013.01); *A61B 2562/164* (2013.01); *A61B 2562/166* (2013.01)

(58) Field of Classification Search
None
See application file for complete search history.

(56) References Cited

U.S. PATENT DOCUMENTS

| 4,793,362 A | * | 12/1988 | Tedner | A61B 5/0535 600/547 |
| 5,063,937 A | * | 11/1991 | Ezenwa | A61B 5/0535 600/536 |
| 6,843,771 B2 | * | 1/2005 | Lo | A61B 5/02438 600/459 |

(Continued)

OTHER PUBLICATIONS

R. S. H. Istepanian, B. Woodward, "Microcontroller-Based Underwater Acoustic ECG Telemetry System," IEEE Transactions on Information Technology in Biomedicine, vol. 1, No. 2, pp. 150-154, 1997. (Year: 1997).*

*Primary Examiner* — Matthew Kremer
*Assistant Examiner* — Samuel C Kim
(74) *Attorney, Agent, or Firm* — Georgiy L. Khayet

(57) ABSTRACT

Systems and methods for bioimpedance measurement are provided. An example system includes a strap for carrying a smart watch on a wrist of a user, a bioimpedance measurement module, and an acoustic generator embedded into the strap. The bioimpedance measurement module is configured to measure an impedance of a tissue of the user. The acoustic generator is further configured to generate an acoustic signal modulated to carry data including the impedance. The acoustic signal can be sensed by an acoustic sensor of the smart watch. The smart watch may include an application for sensing the acoustic signal and for converting the sensed acoustic signal into a value for the impedance.

20 Claims, 8 Drawing Sheets

(56) References Cited

U.S. PATENT DOCUMENTS

| | | | |
|---|---|---|---|
| 2006/0167374 A1* | 7/2006 | Takehara | A61B 5/0537 600/547 |
| 2007/0043303 A1* | 2/2007 | Osypka | A61B 5/7239 600/547 |
| 2007/0208232 A1* | 9/2007 | Kovacs | A61B 5/02055 600/300 |
| 2009/0076336 A1* | 3/2009 | Mazar | A61B 5/0402 600/300 |
| 2009/0093732 A1* | 4/2009 | Kasahara | A61B 5/4869 600/547 |
| 2011/0251817 A1* | 10/2011 | Burns | A61B 5/0531 702/104 |
| 2013/0331678 A1* | 12/2013 | Lading | A61B 5/7278 600/393 |
| 2015/0145673 A1* | 5/2015 | Choi | A61B 5/6843 340/539.12 |
| 2016/0195484 A1* | 7/2016 | Emery | G01R 19/0092 702/65 |
| 2018/0035910 A1* | 2/2018 | Conchell Ano | A61B 5/0531 |
| 2018/0220923 A1* | 8/2018 | Shim | G06F 1/163 |
| 2018/0368701 A1* | 12/2018 | Vule | A61B 5/0205 |

* cited by examiner

SMART WATCH STRAP FOR BIOIMPEDANCE MEASUREMENTS

TECHNICAL FIELD

The present disclosure relates generally to health monitoring, and more particularly, to systems and methods for bioimpedance measurements.

BACKGROUND

Bioimpedance measurements and bioimpedance analysis can be used for estimation of human body composition, and, more specifically, for determining amounts of fat mass and fat free mass of human body, body cell mass, and total body water including extracellular fluid and intracellular fluid. Therefore, bioimpedance measurements are widely used in monitoring of health statuses and disease prognoses. Performing continuous daily or weekly bioimpedance measurements in a convenient manner may be specifically useful for detecting early warnings concerning degrading health statuses of humans.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Provided are systems and methods for bioimpedance measurements. Some embodiments of the present disclosure provide a strap for a smart watch and a bioimpedance measurement module embedded into the strap. The strap can be used by a user for hand-to-hand bioimpedance measurements. The strap may transmit measured bioimpedance to the smart watch via a high frequency acoustic generator.

According to one example embodiment, a system for bioimpedance measurement is provided. The system may include a strap for carrying a smart watch on a wrist of a user. The system may include a bioimpedance measurement module embedded into the strap. The bioimpedance measurement module can be configured to measure impedance of a tissue of the user. The system may also include an acoustic generator embedded into the strap and coupled with the bioimpedance measurement module. The acoustic generator can be configured to generate an acoustic signal modulated to carry data, including the impedance. The smart watch may include an acoustic sensor to sense the acoustic signal. The smart watch may include a processor coupled to the acoustic sensor. The smart watch may also include a memory storing an application comprising processor-executable codes. Upon executing the processor-executable codes the processor is configured to convert the sensed acoustic signal into a value for the impedance.

The acoustic generator can be configured to generate a first signal to transmit a zero bit of the data and a second signal to transmit a nonzero bit of the data.

The system may further include a first communication unit embedded into the strap and coupled with the bioimpedance measurement module. The communication unit can be configured to transmit the data including the impedance via a wireless network protocol. The smart watch may further include a second communication unit configured to receive the data including the impedance via the wireless network protocol. The wireless network protocol can be one of Bluetooth™ protocol or near field communication protocol.

The bioimpedance measurement module may include a microprocessor, a pulse width modulation (PWM) circuit, and an analog-to-digital converter (ADC). The PWM circuit can be configured to generate a PWM signal. The PWM signal can be used to generate an alternating current (AC) electrical signal to run through the tissue of the user. For example, the bioimpedance measurement module may include an output circuit configured to generate, based on the PWM signal, the alternating current (AC) electrical signal. The output circuit can include a low pass filter.

The bioimpedance measurement module may include a first current electrode and a second current electrode configured to provide the AC electrical signal to the tissue of the user. The bioimpedance measurement module may include a first voltage electrode and a second voltage electrode configured to sense a differential voltage on the tissue of the user. The ADC can be configured to measure the differential voltage. For example, the bioimpedance measurement module may include an input circuit configured to output an analog voltage signal representing the differential voltage. The ADC can be configured to convert the analog voltage signal into a discrete signal.

The microprocessor can be configured to analyze the discrete signal to determine the impedance. The microprocessor can be configured to generate the data including the impedance. The microprocessor can be also configured to cause the acoustic generator to generate the acoustic signal modulated to carry the data, including the impedance.

The ADC and the PWM circuit can be integrated into the microprocessor. A sampling frequency of the ADC can be four time higher than a frequency of the AC electrical signal. The microprocessor can be configured to perform an analysis of the discrete signal to determine impedance values for at least two different frequencies. The microprocessor may generate data including the impedance values. The microprocessor may cause the acoustic generator to generate the acoustic signal modulated to carry the data including the impedance values.

The first current electrode and the first voltage electrode can be located on an inner surface of the strap. The second current electrode and the second voltage electrode can be located on an external surface of the strap.

According to another example embodiment, a method for bioimpedance measurement is provided. The method may include providing a strap for carrying a smart watch on a wrist of a user. The smart watch may include an acoustic sensor and a processor. The method may include disposing a bioimpedance measurement module within the strap. The bioimpedance measurement module can be configured to measure an impedance of a tissue of the user. The method may include disposing an acoustic generator within the strap. The acoustic generator can be coupled with the bioimpedance measurement module. The acoustic generator can be configured to generate an acoustic signal modulated to carry data including the impedance. The method may include providing an application for the smart watch. The application may include processor-executable codes causing the acoustic sensor to sense the acoustic signal and the processor to convert the sensed acoustic signal into a value of the impedance.

Additional objects, advantages, and novel features will be set forth in part in the detailed description section of this disclosure, which follows, and in part will become apparent to those skilled in the art upon examination of this specification and the accompanying drawings or may be learned by production or operation of the example embodiments. The objects and advantages of the concepts may be realized and attained by means of the methodologies, instrumentalities, and combinations particularly pointed out in the appended claims.

BRIEF DESCRIPTION OF THE DRAWINGS

Embodiments are illustrated by way of example and not limitation in the figures of the accompanying drawings, in which like references indicate similar elements and, in which.

DETAILED DESCRIPTION

Figure 1:
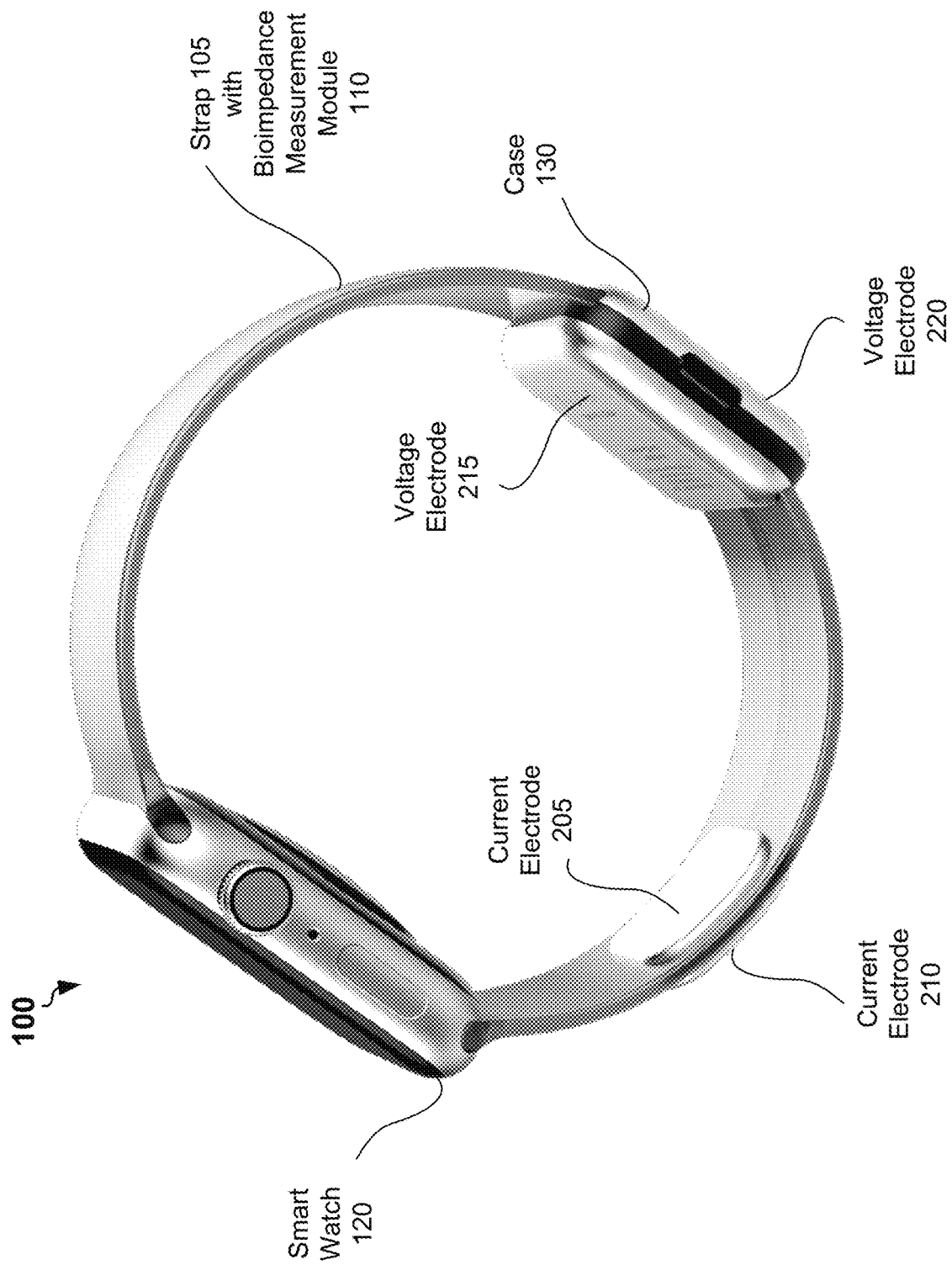
FIG. 1 shows an example system for bioimpedance measurements, according to some embodiments of the present disclosure.

The following detailed description includes references to the accompanying drawings, which form a part of the detailed description. The drawings show illustrations in accordance with example embodiments. These example embodiments, which are also referred to herein as "examples," are described in enough detail to enable those skilled in the art to practice the present subject matter. The embodiments can be combined, other embodiments can be utilized, or structural, logical, and electrical changes can be made without departing from the scope of what is claimed. The following detailed description is, therefore, not to be taken in a limiting sense, and the scope is defined by the appended claims and their equivalents.

The present disclosure provides methods and systems for bioimpedance measurements. Some embodiments of the present disclosure provide a strap for a smart watch. The strap may include a bioimpedance measurement module designed for performing bioimpedance measurements and transmitting measured impedance data to the smart watch. Some embodiments of the present disclosure provide a convenient way for obtaining daily bioimpedance data that can be used for early detections of diseases and provide early warnings about degrading health status of a user of the strap.

According to one example embodiment, an example system for bioimpedance measurement may include a strap for carrying a smart watch on a wrist of a user. The system may include a PWM circuit embedded into the strap and configured to generate a PWM signal. The system may further include an output circuit embedded into the strap and configured to generate, based on the PWM signal, an alternating current (AC) electrical signal. The system may further include a first current electrode and a second current electrode embedded into the strap and configured to provide the AC electrical signal to a tissue of the user. The system may further include a first voltage electrode and a second voltage electrode embedded into the strap and configured to sense a differential voltage on the tissue of the user. The first current electrode and the first voltage electrode can be located on an inner surface of the strap. The second current electrode and the second voltage electrode can be located on an outer surface of the strap allowing the user to attach the second current electrode and the second voltage electrode by the palm of the other hand or by fingers.

The system may include an input circuit configured to output an analog voltage signal representing the differential voltage between the first voltage electrode and the second voltage electrode. The system may include an ADC embedded into the strap and configured to convert the analog voltage signal into a discrete signal. The system may further include a microprocessor embedded into the strap and configured to analyze the discrete signal to determine an impedance of the tissue of the user. The microprocessor may further generate data including the impedance. The system may further include an acoustic generator embedded into the strap and configured to generate an acoustic signal modulated to carry the data, including the impedance. The smart watch may include an acoustic sensor to sense the acoustic signal. The smart watch may include a processor coupled to the acoustic sensor and a memory storing an application comprising processor-executable codes. Upon executing the processor-executable codes the processor can convert the sensed acoustic signal into a value for the impedance.

Referring now to the drawings, FIG. 1 shows an example system 100 for bioimpedance measurement, according to some embodiments of the present disclosure. The system 100 may include a smart watch 120 and a strap 105 for carrying the smart watch on a wrist of a user. Instead of the strap 105, the system 100 may include a band or a bracelet for carrying the smart watch on the wrist of the user.

The system 100 may further include a bioimpedance measurement module 110 embedded into the strap 105. The bioimpedance measurement module 110 may be partially installed into the case 130. The bioimpedance measurement module 110 may include a first current electrode 205, a second current electrode 210, a first voltage electrode 215, and a second voltage electrode 220.

In example of FIG. 1, the first current electrode 205 and the first voltage electrode 215 are located on an inner surface of the strap 105. When the user wears the strap 105 on a hand (at a wrist), the first current electrode 205 and the first voltage electrode 215 are in permanent contact with a tissue of the hand of the user. The first current electrode 205 and the first voltage electrode 215 can be separated by at least 4 millimeters from each other. Area of a surface of the first current electrode 205 and area of a surface of the first voltage electrode 215 can be at least 4 square centimeters. The second current electrode 210 and the second voltage electrode 220 can be located on an outer surface of the strap 105. A user may place a palm or fingers of another hand to bring tissue of another hand in contact with the second current electrode 210 and the second voltage electrode 220 during bioimpedance measurement.

The first current electrode 205, the second current electrode 210, the first voltage electrode 215, and the second voltage electrode 220 can be flexible and can be made of an electrical conductor resistance to corrosion, for example a galvanized copper coil. In other embodiments, the locations of the first current electrode 205 and the second current electrode 210 on the inner surface of the strap 105 can be different from the locations depicted in FIG. 1. Similarly, the first voltage electrode 215, and the second voltage electrode 220 on the outer surface of the strap 105 can be different from the locations depicted in FIG. 1.

Figure 2:
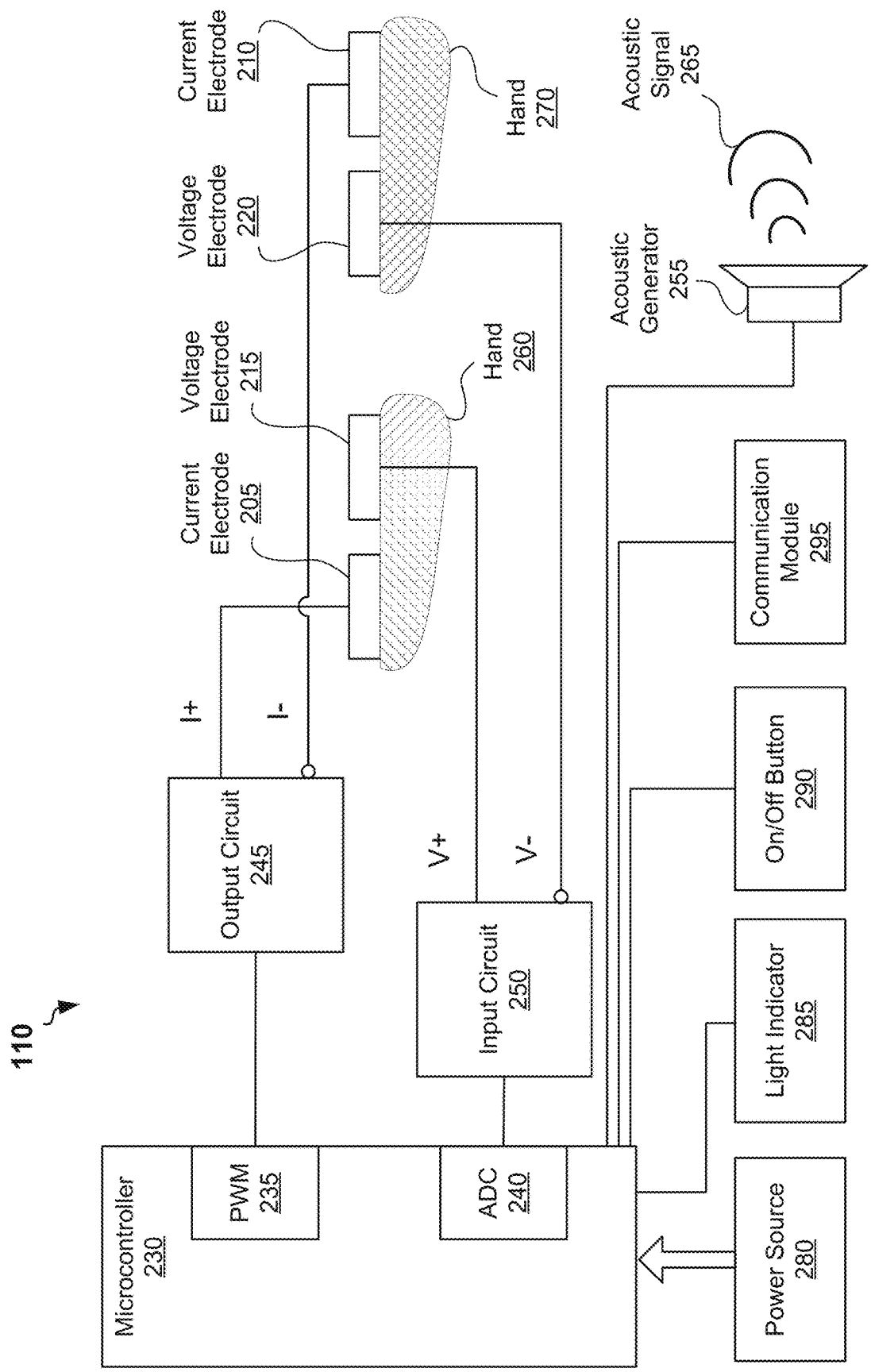
FIG. 2 is a block diagram of an example bioimpedance measurement module, according to some example embodiments.

FIG. 2 is a block diagram of an example bioimpedance measurement module 110, according to some example embodiments. FIG. 2 provides more details of the bioimpedance measurement module 110 shown partially in FIG. 1. The bioimpedance measurement module 110 may include a microprocessor 230, a PWM circuit 235, an ADC 240, an output circuit 245, a power source 280, a light indicator 285, and on/off button 290. The bioimpedance measurement module 110 may further include a first current electrode 205, a second current electrode 210, a first voltage electrode 215, and a second voltage electrode 220 as shown in FIG. 1. The bioimpedance measurement module 110 may be coupled with an acoustic generator 225. The acoustic generator 225 can be also embedded into the strap 105 shown in FIG. 1. The bioimpedance measurement module 110 may be also coupled with a communication module 295. The communication module 225 can be embedded into the strap 105 shown in FIG. 1. The bioimpedance measurement module 110 and the strap 105 may include additional or other components necessary for operations and communications of the bioimpedance measurement module 110. In other embodiments, bioimpedance measurement module 110 and the strap 105 may include fewer components that perform similar or equivalent functions to those depicted in FIG. 2 and FIG. 1.

In some embodiments, the PWM circuit 235 and ADC 240 can be integrated into the microcontroller 230. It is important for operation of the bioimpedance measurement module 110 to synchronize operations of the PWM circuit 235 and operations of ADC 240.

In some embodiments, PWM circuit 235 can be configured to generate a PWM signal. The PWM signal may have a duty cycle of 50 percent, that is the PWM signal comprises true square waves. In certain embodiments, the frequency of the PWM signal can be selected to be substantially higher than frequency of sampling of the ADC 240.

The output circuit 245 may generate, based on the PWM signal, an alternating current (AC) electrical signal within pre-determined amplitudes of voltage and current. In some embodiments, the output circuit may include a low pass filter to generate a sinusoidal AC electrical signal.

The AC electrical signal can be delivered to tissue of the user via the first current electrode 205 and the second current electrode 210 located on opposite surfaces of the strap 105 as shown in FIG. 1. If the strap 105 is worn on a hand 260 of a user, then during bioimpedance measurements the user can touch the second current electrode 210 with a palm or a finger of another hand 270 to allow the AC current to flow through tissue of body of the user. At the same time, the user should touch the second voltage electrode 220 with the hand 270 to allow the first voltage electrode 215 and the second voltage electrode 220 to sense differential voltage from two location of tissue of the user.

The input circuit 250 may further generate an analog voltage signal representing the voltage difference sensed by the voltage electrodes. The input circuit 250 may include an amplifier to measure the differential voltage.

The ADC 240 may be configured to generate, based on the analog voltage signal, a discrete signal. The microprocessor 230 may further perform analysis of the discrete signal to determine an amplitude and phase of the analog voltage signal. The microprocessor 230 can be further configured to determine impedance based on the amplitude and a phase of the analog voltage signal and an amplitude and a phase of the AC electrical signal. In some embodiments, a frequency of sampling of ADC 240 can be four times higher than a frequency of the analog voltage signal. For example, frequency of sampling can be selected to be 200 kilohertz for the frequency of 50 kilohertz of the analog voltage signal.

The amplitude and phase of the analog voltage signal can be determined by one of the following methods.

Method 1

According to some embodiments of the present disclosure, the PWM circuit 235 can be configured to generate a PWM signal with a frequency equal to an inverse of a conversion time of the ADC 240. The input circuit 250 can be configured to apply a first order resistor-capacitor filter to the differential voltage sensed by the electrodes 215 and 220. For example, a resolution of the ADC 240 can be at least 12 bits and the ADC 240 can be configured to operate at frequency of 200 kilohertz per second.

A frequency of the PWM signal can be 50 kilohertz and a duty cycle of the PWM signal can be 50 percent. Thus, a frequency of sampling of the ADC 240 is four times of the frequency of the analog voltage signal (narrow band signal) outputted by the input circuit 250. In this case, each other samples generated by the ADC 240 represent a quadrature of a real part and a quadrature of an imaginary part of the analog voltage signal. An amplitude and a phase of the analog voltage signal can be determined based on the quadrature of the real part and the quadrature of the imaginary part by a Euler formula.

Figure 3:
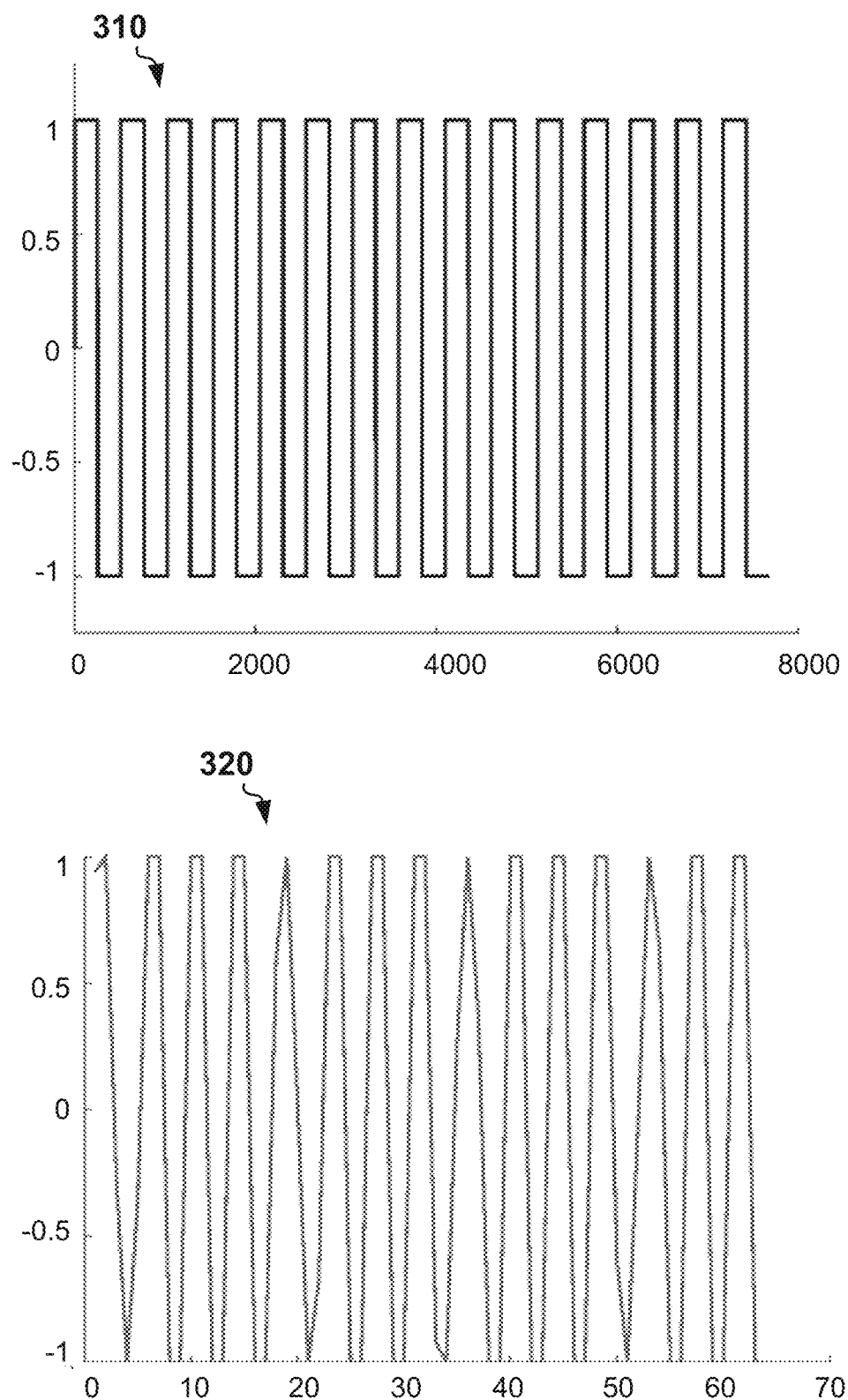
FIG. 3 shows a plot of an example pulse width modulation (PWM) signal and a plot of a signal restored by analog-to-digital converter (ADC) from an analog voltage signal.

FIG. 3 shows a plot 310 of an example PWM signal and a plot 320 of a signal restored by ADC from the analog voltage signal. The shape of the restored signal accounts for ADC analog frequency response. The restored signal is shifted to the zero frequency.

Figure 4:
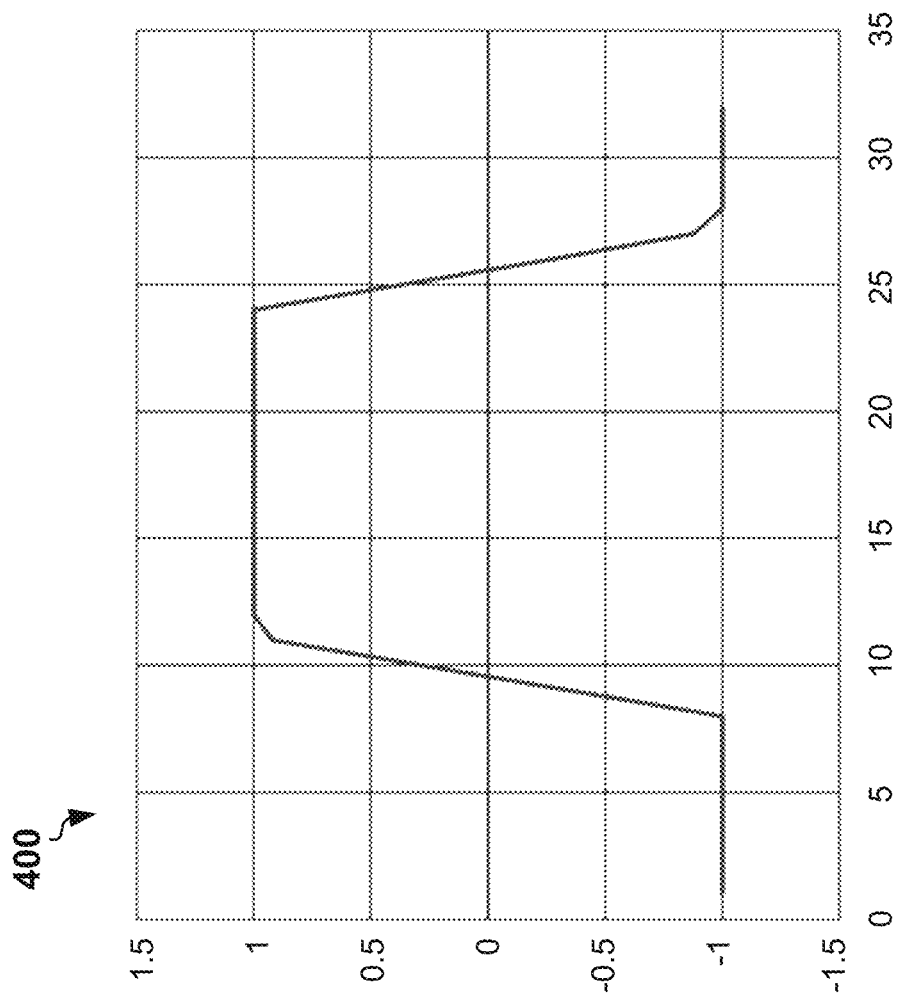
FIG. 4 is a plot of a square wave restored by the ADC from an analog voltage signal.

FIG. 4 show shows a plot 400 an example square wave restored by ADC from the analog voltage signal.

Method 2

In some embodiments, a frequency of PWM signal and a frequency of the sampling by ADC can be selected in a such way to make it possible to perform multi-frequency bioimpedance measurements. In this case the ADC may operate beyond a first Nyquist zone.

Figure 5A:
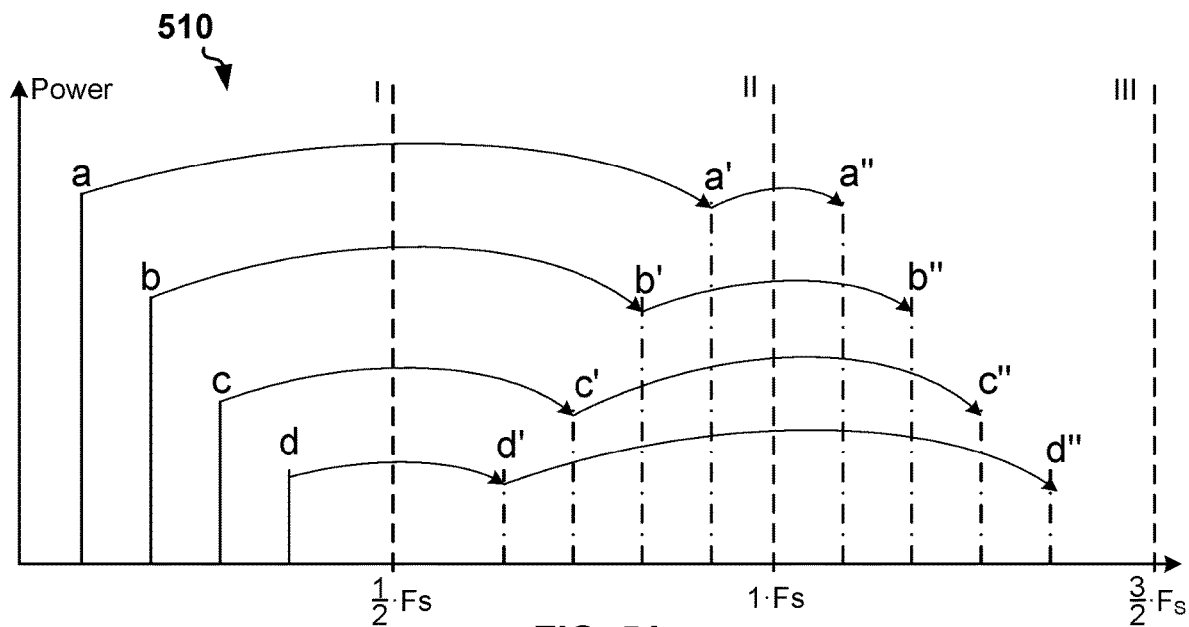
FIG. 5A is a plot of a spectrum of an example discrete periodic signal having frequency components in a single Nyquist zone.

FIG. 5A is a plot of a spectrum 510 of an example discrete signal having all frequency components in a single Nyquist zone. In example of FIG. 5, Fs is a sample rate of ADC. The spectrum includes four frequency components a, b, c, and d within the first Nyquist zone [0; ½ Fs]. The spectrum 510 signal includes high frequency components in the second and further Nyquist zones. Due to folding, replica of the spectrum 510 occurs in odd numbered Nyquist zones [(k−1) Fs/2; k Fs/2], k=2, 4, . . . . Mirrored replica of the spectrum 510 occur in even numbered Nyquist zones [(k−1) Fs/2; k Fs/2], k=3, 5, . . . .

Figure 5B:
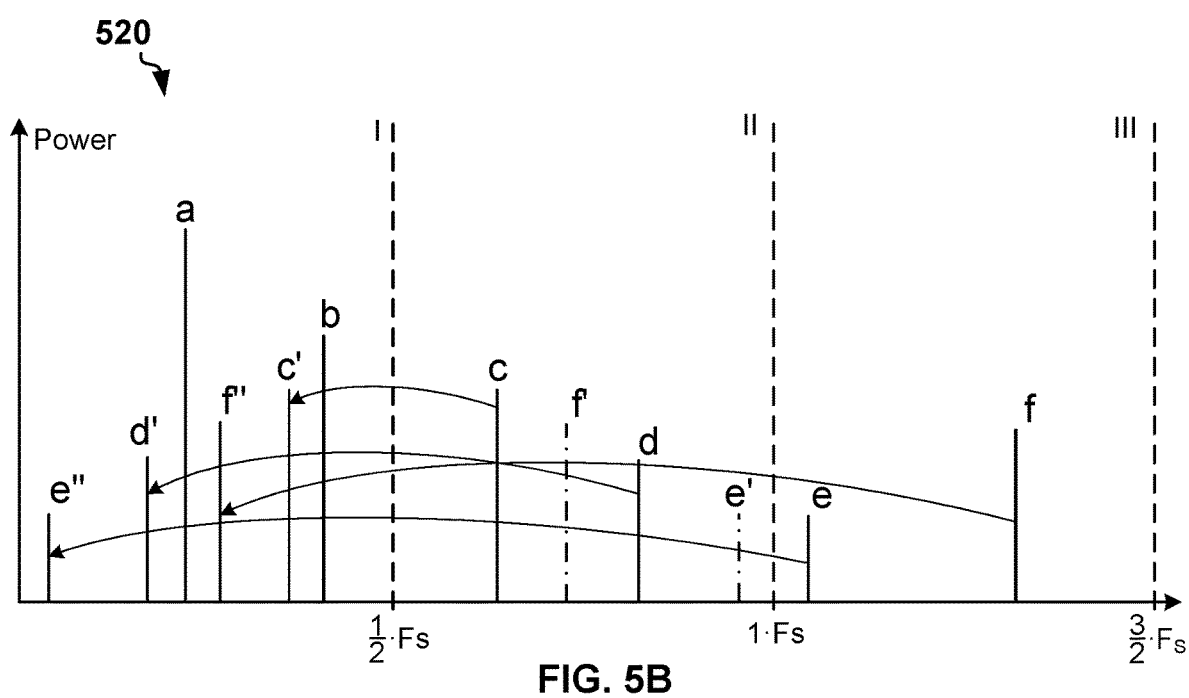
FIG. 5B is a plot of a spectrum of an example discrete periodic signal having frequency components in multiple Nyquist zones.

FIG. 5B is a plot of a spectrum 520 of an example discrete signal having frequency components in multiple Nyquist zone. In example of FIG. 5B, the spectrum 520 includes frequency components a and b in the first Nyquist zone, frequency components c and d in the second Nyquist zone, and frequency components e and f in the third Nyquist zone. Due to folding, the spectrum 520 may include frequency components e″, d′, f′, and c′ in the first Nyquist zone, which are reflections of the frequency components e, d, f, and b located in the second Nyquist zone and the third Nyquist zone. A shape of a discrete signal having spectrum in multiple Nyquist zones can be restored unambiguously only if there is no aliasing of the frequency components.

A frequency of PWM signal, frequency of AC electrical signal generated based on the PWM signal and a frequency of sampling of ADC can be selected to avoid aliasing of frequency components of the sampled discrete signal due to folding. Complex amplitudes of harmonics of the signal sampled by the ADC can be determined via a fast Fourier transform.

Method 3

According to some other embodiments of the present disclosure, the analog voltage signal outputted by the input circuit 250 can be discretized by a stroboscopic sampling. In this case the ADC may operate beyond a first Nyquist zone. A frequency of a discrete signal produced by ADC can be equal to difference of a frequency of the analog voltage signal (which is determined by a frequency of PWM signal) and a frequency of ADC sampling.

Figure 6:
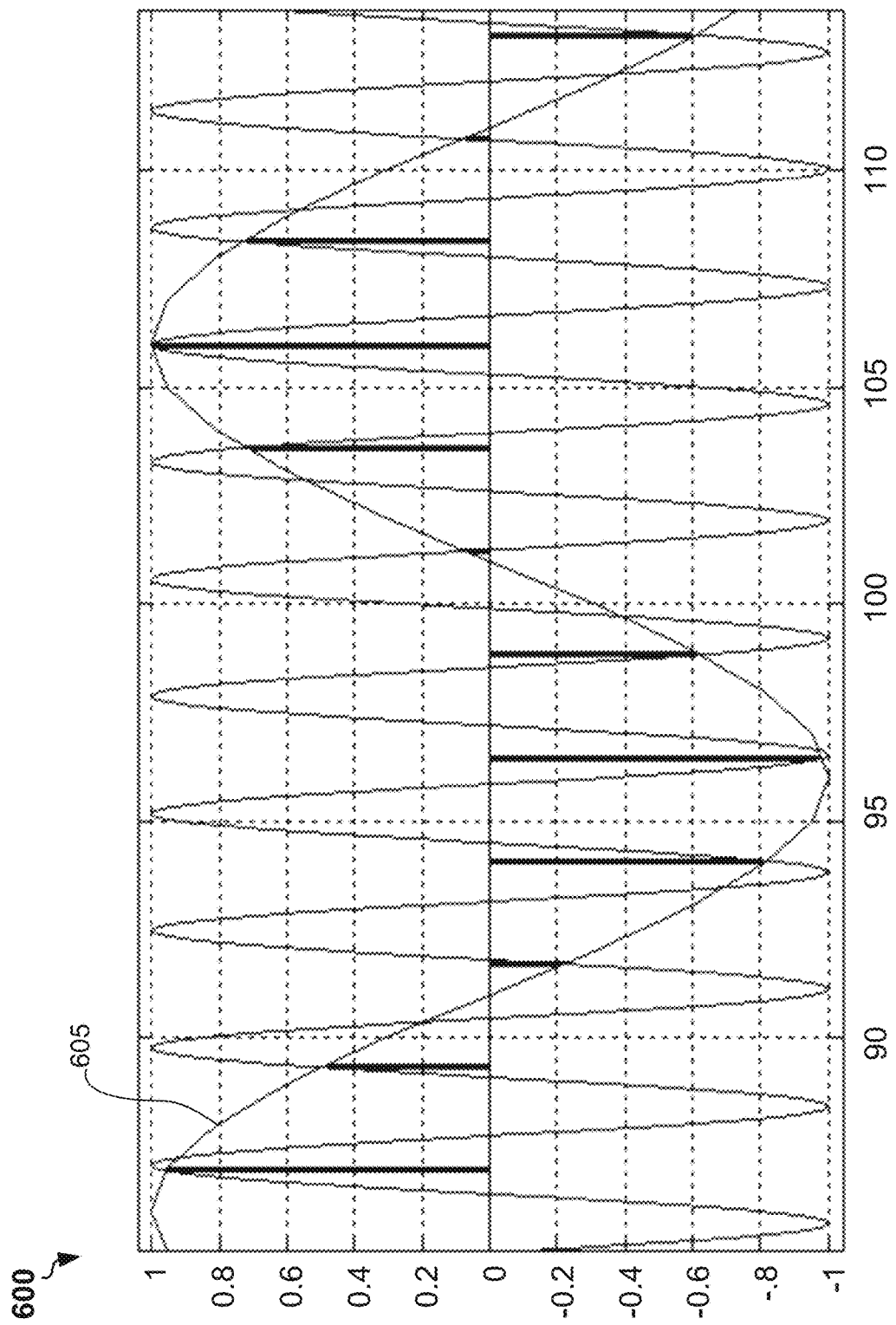
FIG. 6 shows a plot of stroboscopic discretization of an example analog signal.

FIG. 6 shows a plot 600 a stroboscopic sampling of an example analog voltage signal 605 (a test signal). In the stroboscopic sampling, M samples of ADC correspond to N waves of the analog voltage signal 605 (test signal), wherein M and N are integers that do not have common factors. For example, if a wave of the PWM signal includes 512 samples at a microprocessor clock frequency of 24 megahertz, then a frequency of analog voltage signal is 24 megahertz/512=46,875 kilohertz. The sampling frequency of ADC can be selected in a such way that each 64 samples of ADC correspond to 15 waves of the PWM signal. Because number 64 and 15 do not have common factors, ADC sampling can be carried out for different phase of waves of PWM signal. Correspondingly a wave of the PWM signal can be restored using 64 samples. This corresponds to a virtual frequency of discretization equal to 46,875 kilohertz×64=3 megahertz. A complex amplitude of a first harmonics of the sampled signal can be determined via a fast Fourier transform or Goertzel algorithm. Similarly, packets including 1, 3, 5, and 45 waves of PWM signal can be discretized using 64 samples to obtain a set of frequencies 3.125 kilohertz, 9.375 kilohertz, 15.625 kilohertz, and 234,375 kilohertz that can be used in bioimpedance measurement and multi-frequency bioimpedance analysis (BIA).

Referring back to FIG. 2, the microprocessor 230 may further generate data including a real part of impedance and an imaginary part of impedance. For example, the microprocessor may generate a 32-bit binary number, wherein the first 16 bits can be used to represent the real part of impedance and the second 16 bits can be used to represent the imaginary part of the impedance. In the embodiments with the bioimpedance measurement module 110 configured to perform multi-frequency BIA, the data may include records in a binary format. Each record may include a real part of impedance, an imaginary part of impedance, and a frequency of harmonics corresponding to the impedance.

In some embodiments, the acoustic generator 225 can be configured to generate, based on the data including the impedance, an acoustic signal 265. The acoustic signal may comprise a series of acoustic signals, wherein each of the series of the acoustic signals is a first signal or a second signal. The first signal may correspond to a zero bit of the data and the second signal may correspond to a non-zero bit of the data. The first signal may have a first frequency and can be transmitted a first pre-determined time. The second signal may have a second frequency and can be transmitted for a second pre-determined time. For example, the first signal can be a 12 kilohertz acoustic signal and the second signal can be a 15 kilohertz signal.

In some embodiments, the data generated by the bioimpedance measurement module 110 can be transmitted via communication module 210. In various embodiments, the communication module may include a radio module configured to transmit the data using one or more wireless technology standards, including but not limited to a Bluetooth™ standard or Near Field Communication (NFC) standard.

In some embodiments, the light indicator 285 may include a light-emitting diode (LED), for example a red-green-blue (RGB) LED. The color of light of the LED may indicate one of modes of the bioimpedance measurement module 110. For example, the color of light of the RGB LED may indicate one of the following states of the bioimpedance measurement module 110: "performing impedance measurement", "switch on", and "low level of power source".

In some embodiment, the on/off button 290 can be a mechanical button or a sensor button for turning the bioimpedance measurement module 110 on and off. In embodiments with the sensor button, the bioimpedance measurement module 110 can be configured to switch on only when the user touches the sensor button for at least 5 seconds in order to avoid false start up due to accidental touches. The on/off button 290 can be integrated into one of the second current electrode 210 or the second voltage electrode 220 located on outer surface of the strap 105. In this case, the bioimpedance measurement module 110 can start up when the user touches the electrodes on the outer surface of the strap 105.

In some embodiments, the power source 280 may include a non-rechargeable battery, for example a lithium battery. The battery may include a capacity enough for performing bioimpedance measurements two times each day for six months, wherein duration of each of the bioimpedance measurements does not exceed 10 seconds. In other embodiments, the power source 280 may include a rechargeable battery. In these embodiments, the strap 110 may include two electrical contacts at the surface to provide electrical current from a charger to the rechargeable battery.

Figure 7:
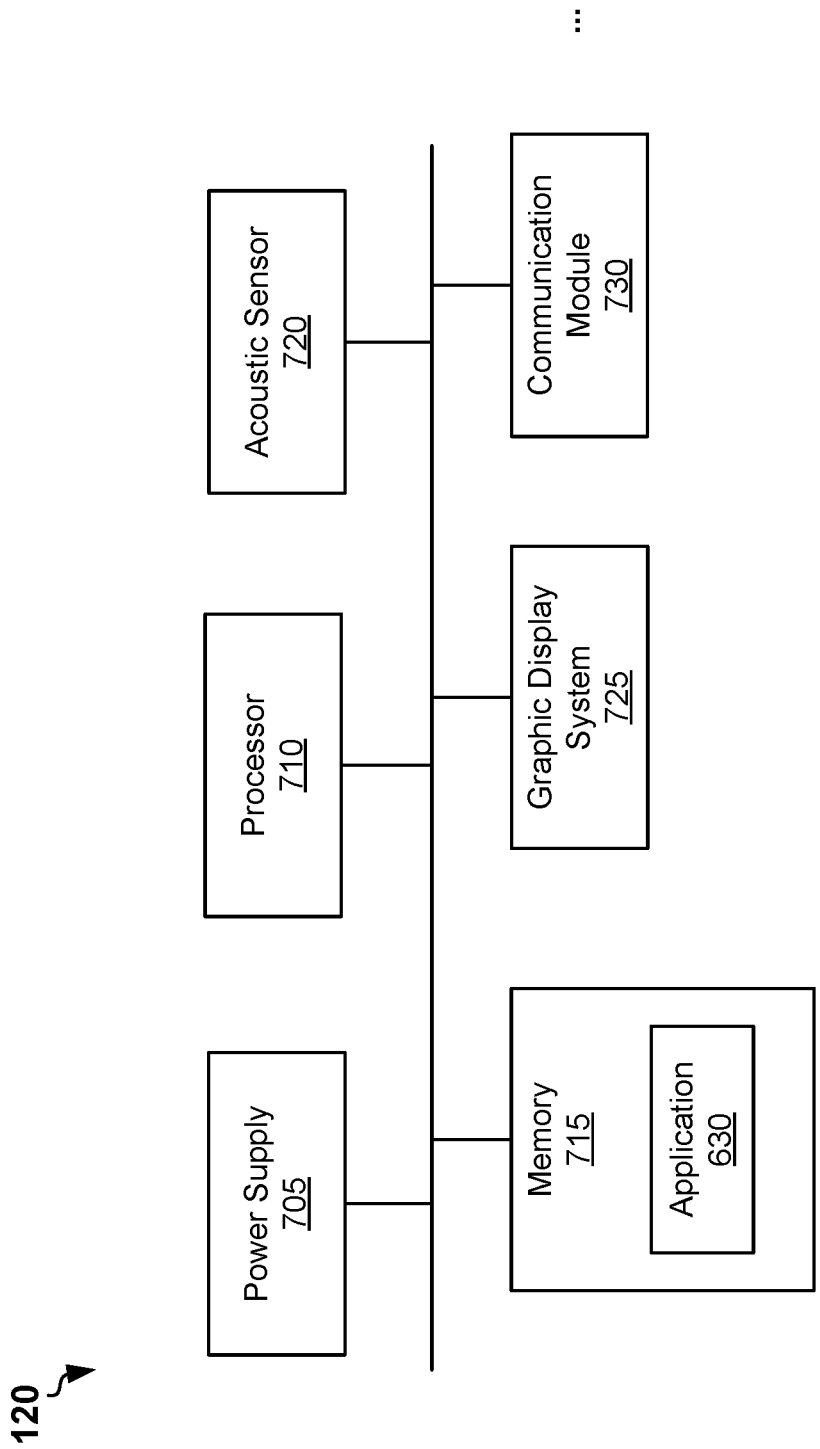
FIG. 7 is a block diagram of an example smart watch that can be used to implement a method for bioimpedance measurements, according to an example embodiment.

FIG. 7 is a block diagram of example smart watch 120, according to some example embodiments. The smart watch 120 may include a power supply 705, a processor 710, an acoustic sensor 720, a memory 715, and a graphic display system 725. The smart watch 120 may also include a communication module 730. The smart watch 120 may also include additional or other components necessary for operations of the smart watch 120. In other embodiments, the smart watch 120 may include fewer components that perform similar or equivalent functions to those depicted in FIG. 6. In various embodiments, the smart watch 120 can be an Apple Watch™ or one of other smart watches or analogues devices available on the market.

The acoustic sensor 720 can be configured to sense acoustic signal 265 generated by the acoustic generator 255 (shown in FIG. 2). In some embodiments, the communication module 730 may receive data transmitted by the communication module 295 (shown in FIG. 2). In various embodiments, the communication module 730 may include a wireless radio module configured to receive data using one or more wireless technology standards, including but not limited to a Bluetooth™ standard or Near Field Communication (NFC) standard.

The memory 715 may store an application 630. The application 630 may include a processor-executable codes. Upon executing the application 630, the processor 710 can be configured at least to analyze the signal sensed by the acoustic sensor 620 and convert the sensed signal into a value of the impedance. Additionally, or alternatively, the processor 710 may receive the value for the impedance from the communication module 730. In some embodiments, the application 630 may allow a user of the smart watch 120 to select a channel of receiving the data from the strap 105. The channels may include receiving the data via the acoustic sensor and receiving the data via the communication module using a specific communication protocol, for example a Bluetooth™ or NFC. The value of the impedance can be stored in the memory 715, for example in database including records of values of impedance and date and time of the bioimpedance measurements are carried out. The values of the impedance can be made available to other applications running on the smart watch 120 or further computer devices for performing further bioimpedance analysis. In embodiments with the bioimpedance measurement module 110 configured to perform multifrequency BIA, the data include values of impedance determined at multiple frequencies and values of the frequencies.

It should be noted, that the microprocessor 230 may be configured to transmit, via the acoustic generator 255, further data other than the value of the impedance. For example, the further data may include a level of charge of the battery in strap 105 and an indication that bioimpedance measurements by the strap 105 have been started. Upon receiving the further data via the acoustic sensor 320, the processor 310 may display, via the graphical display system 325, the level of charge and a progression bar indicating time of process of the bioimpedance measurements. The time of completing of the bioimpedance measurements can be pre-determined. For example, the time of completing of the bioimpedance measurements can be 10 seconds.

Figure 8:
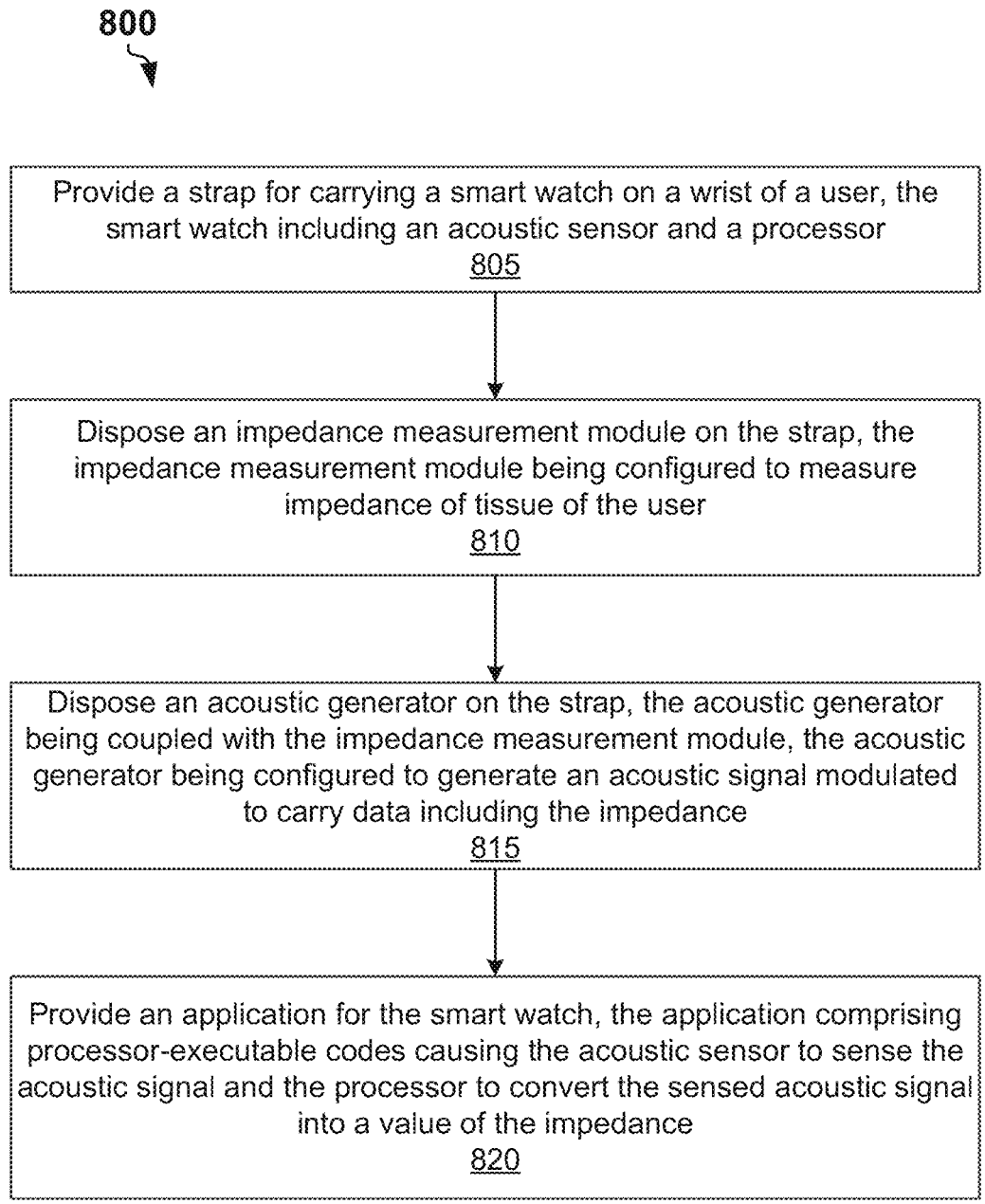
FIG. 8 is a flow chart of example method for bioimpedance measurements, according to some example embodiments.

FIG. 8 is a flow chart of a method 800 for bioimpedance measurements, according to some example embodiments. The method 800 may commence in block 810 with providing a strap for carrying a smart watch on a wrist of a user. The smart watch may include an acoustic sensor and a processor.

In block 820, the method 800 may include disposing a bioimpedance measurement module within the strap. The bioimpedance measurement module can be configured to measure an impedance of a tissue of the user. The bioimpedance measurement module may include a PWM circuit configured to generate a PWM signal. The bioimpedance measurement module may include an output circuit configured to generate, based on the PWM signal, an alternating current (AC) electrical signal. The bioimpedance measurement module may include a first current electrode and a second current electrode configured to provide the AC electrical signal to the tissue of the user. The bioimpedance measurement module a first voltage electrode and a second voltage electrode configured to sense a differential voltage on the tissue of the user. The bioimpedance measurement module may include an input circuit configured to output an analog voltage signal representing the differential voltage. The bioimpedance measurement module may include an ADC configured to convert the analog voltage signal into a discrete signal. The bioimpedance measurement module may include a microprocessor. The microprocessor may be configured to analyze the discrete signal to determine the impedance. The microprocessor may be configured to generate data including the impedance.

In block 830, the method 800 may include disposing an acoustic generator within the strap. The acoustic generator can be coupled with the bioimpedance measurement module. The acoustic generator can be configured to generate an acoustic signal modulated to carry the data including the impedance. The acoustic generator can be configured to generate a first signal to transmit a zero bit of the data and a second signal to transmit a nonzero bit of the data.

In block 840, the method 800 may include providing an application for the smart watch. The application may include processor-executable codes causing the acoustic sensor of the smart watch to sense the acoustic signal and the processor of the smart watch to convert the sensed acoustic signal to into a value of the impedance.

Thus, systems and methods for bioimpedance measurements are described. Although embodiments have been described with reference to specific exemplary embodiments, it will be evident that various modifications and changes can be made to these exemplary embodiments without departing from the broader spirit and scope of the present application. Accordingly, the specification and drawings are to be regarded in an illustrative rather than a restrictive sense.

What is claimed is:

1. A system for bioimpedance measurement, the system comprising:
    a smart watch and a strap for carrying the smart watch on a wrist of a user;
    a bioimpedance measurement module embedded into the strap, the bioimpedance measurement module being configured to measure values of impedance of a tissue of the user, wherein the bioimpedance measurement module is configured to measure the values of impedance by:
        providing an alternating current (AC) electrical signal to the tissue of the user, the AC electrical signal being generated based on a pulse width modulation (PWM) signal of a pre-determined frequency, wherein the pre-determined frequency of the PWM signal is kept unchanged during the measuring;
        sensing an analog voltage signal representing a voltage difference on the tissue of the user, the voltage difference being responsive to the AC electrical signal;
        converting the analog voltage signal to a discrete signal; and
        analyzing the discrete signal to determine the values of impedance, wherein the values of impedance include a first impedance value and a second impedance value, the first impedance value corresponding to a first frequency component of the discrete signal and the second impedance value corresponding to a second frequency component of the discrete signal;
    an on/off button located on an external surface of the strap, the on/off button being configured for turning the bioimpedance measurement module on and off, wherein the bioimpedance measurement module includes at least one electrode integrated into the on/off button; and
    an acoustic generator embedded into the strap and coupled with the bioimpedance measurement module, the acoustic generator being configured to generate an acoustic signal to carry data including the values of impedance, wherein the acoustic generator generates a first signal to transmit a zero bit of the data and a second signal to transmit a nonzero bit of the data, the first signal having a first frequency and the second signal having a second frequency; and wherein the smart watch comprises:
an acoustic sensor to sense the acoustic signal;
a processor coupled to the acoustic sensor; and
a memory storing an application comprising processor-executable codes, wherein,
upon executing the processor-executable codes, the processor is to convert the sensed acoustic signal into the values of impedance.

2. The system of claim 1, wherein the first signal is transmitted for a first pre-determined time and the second signal is transmitted for a second pre-determined time.

3. The system of claim 1, further comprising a first communication unit embedded into the strap and coupled with the bioimpedance measurement module, the communication unit being configured to transmit the data including the values of impedance via a wireless network protocol; and wherein the smart watch further includes a second communication unit configured to receive the data including the values of impedance via the wireless network protocol.

4. The system of claim 3, wherein the wireless network protocol is a near field communication protocol.

5. The system of claim 1, wherein the bioimpedance measurement module comprises:
a PWM circuit configured to generate the PWM signal;
an output circuit configured to generate, based on the PWM signal, the AC electrical signal;
a first current electrode and a second current electrode configured to provide the AC electrical signal to the tissue of the user;
a first voltage electrode and a second voltage electrode configured to sense the voltage difference on the tissue of the user;
an input circuit configured to output the analog voltage signal representing the voltage difference between the first voltage electrode and the second voltage electrode;
an analog-to-digital converter (ADC) configured to convert the analog voltage signal into the discrete signal; and
a microprocessor configured to:
analyze the discrete signal to determine the values of impedance;
generate the data including the values of impedance; and
cause the acoustic generator to generate the acoustic signal to carry the data including the values of impedance.

6. The system of claim 5, wherein the ADC and the PWM circuit are integrated into the microprocessor.

7. The system of claim 5, wherein the output circuit includes a low pass filter.

8. The system of claim 5, wherein the ADC is configured such that a sampling frequency of the ADC is four times higher than a pre-determined frequency of the AC electrical signal generated based on the PWM signal.

9. The system of claim 5, wherein the ADC is configured such that a sampling frequency of the discrete signal is a difference of the pre-determined frequency of the PWM signal and a sampling frequency of the ADC.

10. The system of claim 5, wherein:
the first current electrode and the first voltage electrode are located on an inner surface of the strap; and
the second current electrode and the second voltage electrode are located on an external surface of the strap.

11. A method for bioimpedance measurement, the method comprising:
providing a smart watch and a strap for carrying the smart watch on a wrist of a user, the smart watch including an acoustic sensor and a processor;
disposing a bioimpedance measurement module within the strap, the bioimpedance measurement module being configured to measure values of impedance of a tissue of the user, wherein the measuring of the values of impedance includes:
providing an alternating current (AC) electrical signal to the tissue of the user, the AC electrical signal being generated based on a pulse width modulation (PWM) signal of a pre-determined frequency, wherein the pre-determined frequency of the PWM signal is kept unchanged during the measuring;
sensing an analog voltage signal representing a voltage difference on the tissue of the user, the voltage difference being responsive to the AC electrical signal;
converting the analog voltage signal to a discrete signal; and
analyzing the discrete signal to determine the values of impedance, wherein the values of impedance include a first impedance value and a second impedance value, the first impedance value corresponding to a first frequency component of the discrete signal and the second impedance value corresponding to a second frequency component of the discrete signal;
disposing an on/off button on an external surface of the strap, the on/off button being configured for turning the bioimpedance measurement module on and off, wherein the bioimpedance measurement module includes at least one electrode integrated into the on/off button;
disposing an acoustic generator within the strap, the acoustic generator being coupled with the bioimpedance measurement module, the acoustic generator being configured to generate an acoustic signal to carry data including the values of impedance, wherein the acoustic generator generates a first signal to transmit a zero bit of the data and a second signal to transmit a nonzero bit of the data, the first signal having a first frequency and the second signal having a second frequency; and
providing an application for the smart watch, the application comprising processor-executable codes causing:
the acoustic sensor to sense the acoustic signal; and
the processor to convert the sensed acoustic signal into the values of the impedance.

12. The method of claim 11, wherein the first signal is transmitted for a first pre-determined time and the second signal is transmitted for a second pre-determined time.

13. The method of claim 11, further comprising disposing a first communication unit onto the strap and coupling the first communication unit with the bioimpedance measurement module, the first communication unit being configured to transmit the data including the values of impedance via a wireless network protocol to a second communication unit disposed into the smart watch.

14. The method of claim 13, wherein the wireless network protocol is a near field communication protocol.

15. The method of claim 11, wherein the bioimpedance measurement module comprises:
a PWM circuit configured to generate the PWM signal;

an output circuit configured to generate, based on the PWM signal, the AC electrical signal;
a first current electrode and a second current electrode configured to provide the AC electrical signal to the tissue of the user;
a first voltage electrode and a second voltage electrode configured to sense the voltage difference on the tissue of the user;
an input circuit configured to output the analog voltage signal representing the voltage difference;
an analog-to-digital converter (ADC) configured to convert the analog voltage signal into the discrete signal; and
a microprocessor configured to:
 analyze the discrete signal to determine the values of impedance;
 generate the data including the values of impedance; and
 cause the acoustic generator to generate the acoustic signal to carry the data including the values of impedance.

16. The method of claim 15, wherein the ADC and the PWM circuit are integrated into the microprocessor.

17. The method of claim 15, wherein a sampling frequency of the ADC is four times higher than a pre-determined frequency of the AC electrical signal generated based on the PWM signal.

18. The method of claim 15, wherein a sampling frequency of the discrete signal is a difference of the pre-determined frequency of the PWM signal and a sampling frequency of the ADC.

19. The method of claim 15, wherein:
the first current electrode and the first voltage electrode are located on an inner surface of the strap;
the second current electrode and the second voltage electrode are located on an external surface of the strap; and
the first current electrode and the first voltage electrode are separated by at least 4 millimeters and an area of the first current electrode and an area of the first voltage electrode are at least 4 square centimeters.

20. A system for bioimpedance measurement, the system comprising:
a smart watch and a strap for carrying the smart watch on a wrist of a user;
a pulse width modulation (PWM) circuit embedded into the strap and configured to generate a PWM signal of a pre-determined frequency;
an output circuit embedded into the strap and configured to generate, based on the PWM signal, an alternating current (AC) electrical signal of a pre-determined frequency, the AC electrical signal to be carried by a first current electrode and a second current electrode;
the first current electrode and the second current electrode embedded into the strap and configured to provide the AC electrical signal to a tissue of the user;
a first voltage electrode and a second voltage electrode embedded into the strap and configured to sense a differential voltage on the tissue of the user, wherein the first current electrode and the first voltage electrode are located on an inner surface of the strap and the second current electrode and the second voltage electrode are located on an external surface of the strap;
an input circuit configured to output an analog voltage signal representing the differential voltage between the first voltage electrode and the second voltage electrode;
an analog-to-digital converter (ADC) embedded into the strap and configured to convert the analog voltage signal into a discrete signal;
a microprocessor embedded into the strap and configured to:
 analyze the discrete signal to determine values of impedance of the tissue of the user, the values of impedance including a first impedance value and a second impedance value, wherein the first impedance value corresponds to a first frequency component of the discrete signal and the second impedance value corresponds to a second frequency component of the discrete signal, wherein the pre-determined frequency of the PWM signal is kept unchanged during the analysis; and
 generate data including the values of impedance;
an on/off button located on the external surface of the strap, the on/off button being configured for turning the system for bioimpedance measurement on or off, wherein at least one of the second current electrode and the second voltage electrode is integrated into the on/off button; and
an acoustic generator embedded into the strap and configured to generate an acoustic signal to carry the data including the values of impedance, wherein the acoustic generator generates a first signal to transmit a zero bit of the data and a second signal to transmit a nonzero bit of the data, the first signal having a first frequency and the second signal having a second frequency; and
wherein the smart watch comprises:
 an acoustic sensor to sense the acoustic signal;
 a processor coupled to the acoustic sensor; and
 a memory storing an application comprising processor-executable codes, wherein upon executing the processor-executable codes the processor is configured to convert the sensed acoustic signal into the values of impedance.

* * * * *